United States Patent [19]

Sheldon

[11] 4,235,785

[45] Nov. 25, 1980

[54] 4-ACETYL-2-ALKOXY-7,7-DIMETHYL-3-OXABICYCLO[4.1.0]HEPTANE

[75] Inventor: Roger A. Sheldon, Amsterdam, Netherlands

[73] Assignee: Shell Oil Company, Houston, Tex.

[21] Appl. No.: 55,856

[22] Filed: Jul. 9, 1979

[30] Foreign Application Priority Data

Jul. 19, 1978 [GB] United Kingdom ............... 30370/78

[51] Int. Cl.$^3$ ........................................... C07D 309/06
[52] U.S. Cl. ............................. 260/345.9 R; 560/124
[58] Field of Search ................................. 260/345.9 R

[56] References Cited

U.S. PATENT DOCUMENTS 3,892,814   7/1975   Raphael et al. ............... 260/345.9 R Primary Examiner—Nicky Chan

[57] ABSTRACT

4-Acetyl-2-alkoxy-7,7-dimethyl-3-oxabicyclo[4.1.0]heptanes are new chemical compounds useful as intermediates for certain pyrethroid esters. They are prepared by ozonolysis of 4-hydroxy-2-carene and reduction of the product formed.

3 Claims, No Drawings

4-ACETYL-2-ALKOXY-7,7-DIMETHYL-3-OXABICYCLO[4.1.0]HEPTANE

BACKGROUND OF THE INVENTION

Field of the Invention

This invention relates to new bicyclic compounds and to a process for the preparation of these new compounds.

SUMMARY OF THE INVENTION

The invention provides a process for the preparation of a 4-acetyl-2-alkoxy-7,7-dimethyl-3-oxabicyclo[4.1.0]heptane, which comprises ozonolysis of 4-hydroxy-2-carene and reduction of the product formed by this ozonolysis, both in the presence of an alkanol. The alkanol preferably has less than 6 and particularly less than 3 carbon atoms per molecule; very good results have been obtained with methanol. The alkoxy group in the compounds prepared according to the invention are the same as those of the alkanol used as a starting material. The alkanol is suitably used as a solvent.

The 4-acetyl-2-alkoxy-7,7-dimethyl-3-oxabicyclo[4.1.0]heptanes having the formula

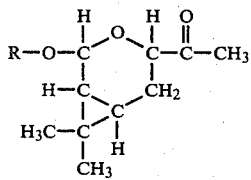

wherein R is an alkyl group containing from 1 to 5 carbon atoms are used as intermediates in the preparation of pyrethroid esters of 2-(2,2-dihalovinyl)-3,3-dimethylcyclopropanecarboxylic acid.

The starting compound 4-hydroxy-2-carene may be prepared as described in Tetrahedron Letters No. 43 (1976) 3861–3864, by isomerization of 3-carene oxide over a solid acid or basic catalyst. This isomerization usually gives a mixture containing 4-hydroxy-2-carene and 4-hydroxy-7,7-dimethyl-3-methylenebicyclo[4.1.0]heptane having the formula

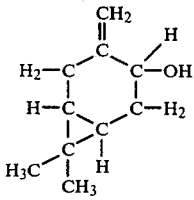

which two compounds are very difficult to separate by distillation.

A feature of the process according to the present invention is that it may be carried out in the presence of 4-hydroxy-7,7-dimethyl-3-methylenebicyclo[4.1.0]heptane, which is simultaneously converted into 4-hydroxy-7,7-dimethylbicyclo[4.1.0]heptanenone having the formula

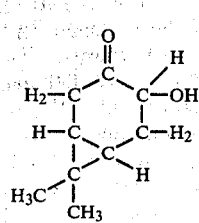

While 4-hydroxy-7,7-dimethylbicyclo[4.1.0]-3-heptanone is difficult to separate by distillation from e.g., 4-acetyl-2-methoxy-7,7-dimethyl-3-oxabicyclo[4.1.0]heptane, it is separated by esterification with succinic anhydride with formation of succinate ester containing one carboxyl group; the latter compound can be washed out with an aqueous solution of a base, leaving 4-acetyl-2-methoxy-7,7-dimethyl-3-oxabicyclo[4.1.0]heptane. If desired, the compounds 4-acetyl-2-methoxy-7,7-dimethyl-3-oxabicyclo[4.1.0]heptane and 4-hydroxy-7,7-dimethylbicyclo[4.1.0]-heptanone can be separated by chromatography on basic alumina.

The 4-acetyl-2-alkoxy-7,7-dimethyl-3-oxabicyclo[4.1.0]heptanes have two asymmetric carbon atoms in the cyclopropane ring and may have the (1R,cis) or the (1S,cis) configuration, regardless of the positions of the alkoxy and the acetyl groups with respect to the six-membered ring; the symbol 1 in the description of the spatial configuration denotes the carbon atom of the cyclopropane ring bound to the CH₂ group. The nomenclature used herein to describe the spatial configurations has been defined by M. Elliott et al. in Nature, 248 (1974) 710–711. Among these two spatial configurations of the 4-acetyl-2-alkoxy-7,7-dimethyl-3-oxabicyclo[4.1.0]heptanes, the (1R,cis) configuration is preferred, because among the four spatial configurations of the pyrethroid esters of 2-(2,2-dihalovinyl-3,3-dimethylcyclopropanecarboxylic acid i.e., (1R,cis), (1R,trans), (1S,cis) and (1S,trans), the (1R,cis) esters have the highest pesticidal activity. Starting from the (1R,cis) isomer of 4-hydroxy-2-carene (the symbol 1 denotes the carbon atom of the cyclopropane ring to which the CH₂ group is bound) the process according to the invention affords compound 1 exclusively in the (1R,cis) configuration.

The ozonolysis can be carried out at a temperature which is not critical and may vary within wide limits; suitable temperatures are in the range of from −100° C. to +50° C., more suitably from −25° C. to +30° C. and particularly of from −5° C. to +20° C. The ozonolysis can be carried out using a gaseous mixture comprising ozone and oxygen. This gaseous mixture may, if desired, be diluted with an inert gas, for example nitrogen, argon or air.

The reduction of the ozonolysis product may be carried out with one or more of the many reducing agents known in the art. This reduction may be carried out catalytically, for example, with hydrogen in the presence of a reduction catalyst. Examples of reduction catalysts are noble metals of Group VIII of the Periodic Table of the Elements, supported on a carrier, such as platinum supported on carbon. Other examples of reducing agents are dimethyl sulphide, potassium iodide, stannous chloride and formaldehyde.

4-Acetyl-2-alkoxy-7,7-dimethyl-3-oxabicyclo[4.1.0]heptanes are novel compounds. The 2-methoxy compound is the preferred pyrethroid intermediate and is hydrolyzed with aqueous acid to yield 2-(2-hydroxy-3-oxobutyl)-3,3-dimethylcyclopropanecarbaldehyde which is readily converted to 1-(2-formyl-3,3-dimethylcyclopropyl)-3-oxo-2-butyl acetate by treatment with, e.g. acetyl halide. This acetate is then added to the product of the reaction of a tri(dialkylamino)phosphine or an alkyl ester of an ortho-phosphorous acid bis(dialkylamide) with a compound generating a dihalocarbene to yield 1-[2-(2,2-dihalovinyl)-3,3-dimethylcyclopropyl]-3-oxo-2-butyl acetate. Oxidation of this compound, e.g. with peroxy acid, yields 2-[2-(2,2-dihalovinyl)-3,3-dimethylcyclopropyl]ethylidene diacetate. These reactions are described in the concurrently filed U.S. patent application Ser. No. 55,854.

The ethylidene diacetate is readily hydrolyzed, e.g. in the presence of acid, to yield 2-(2,2-dihalovinyl-3,3-dimethylcyclopropyl)ethanal as described in the concurrently filed U.S. patent application Ser. No. 55,855. This ethanal is treated with an alkanoic acid anhydride, e.g. in the presence of an amine, to yield a 2-(2,2-dihalovinyl-3,3-dimethylcyclopropyl)vinyl alkanoate which when oxzonized followed by oxidative decomposition yields the free 2-(2,2-dihalovinyl)-3,3-dimethylcyclopropanecarboxylic acid as described in the concurrently filed U.S. patent application Ser. No. 55,858.

ILLUSTRATIVE EMBODIMENT

The present invention is illustrated by the following embodiment which describes the preparation of typical species of the invention and should not be regarded as limiting the invention in any way.

EMBODIMENT 1

A 250 ml round-bottomed flask was charged with (1R,cis)-4-hydroxy-2-carene (77 mmol), (1R,cis)-4-hydroxy-7,7-dimethyl-3-methylenebicyclo[4.1.0]heptane (55 mmol) and water-free methanol (50 ml). A mixture consisting of ozone and oxygen was passed through the liquid in the flask at a rate of 20 mmol of ozone per hour, while the temperature was maintained at 0° C. After 7.5 hours no (1R,cis)-4-hydroxy-2-carene and (1R,cis)-4-hydroxy-7,7-dimethyl-3-methylenebicyclo[4.1.0]heptane could be detected in the flask. The reaction mixture was allowed to adopt a temperature of 20° C. and dimethyl sulphide (145 mmol) was added. The mixture was allowed to stand overnight at 20° C., the solvent was evaporated and the residue formed taken up in n-hexane (50 ml). The solution obtained was washed with two 25-ml portions of water and the washed solution was dried over anhydrous sodium sulphate. Evaporation of the solvent from the dried solution afforded a residue (22.85 g.) which according to gas liquid chromatography analysis consisted of 4-acetyl-2-methoxy-7,7-dimethyl-3-oxabicyclo[4.1.0]heptane (100% (1R,cis), yield 96%, based on the starting amount of 4-hydroxy-2-carene) and 4-hydroxy-7,7-dimethylbicyclo[4.1.0]-3-heptanone (100% (1R,cis), yield 97%, based on the starting amount of 4-hydroxy-7,7-dimethyl-3-methylenebicyclo[4.1.0]heptane). The residue was separated into its components by chromatography on basic alumina. 4-Acetyl-2-methoxy-7,7-dimethyl-3-oxabicyclo[4.1.0]heptane was eluted with n-hexane and 4-hydroxy-7,7-dimethylbicyclo[4.1.0]-3-heptanone with diethyl ether. The Nuclear Magnetic Resonance spectrum of 4-acetyl-2-methoxy-7,7-dimethyl-3-oxabicyclo[4.1.0]heptane showed the following absorptions (using a solution of the compound in carbon tetrachloride and relative to a tetramethylsilane standard):

$\delta = 1.03$ ppm, singlet, intensity 3, C$\underline{H}_3$-C-CH$_3$
$\delta = 1.08$ ppm, singlet, intensity 3, CH$_3$-C-C$\underline{H}_3$
$\delta = 1.30$–0.45 ppm, multiplet, intensity 2, two H atoms bound to the cyclopropane ring.
$\delta = 1.42$ ppm, multiplet, intensity 1, CHC$\underline{H}_2$CH
$\delta = 1.95$ ppm, multiplet, intensity 1, CHC$\underline{H}_2$CH
$\delta = 2.09$ ppm, singlet, intensity 3, C(O)C$\underline{H}_3$
$\delta = 3.30$ ppm, singlet, intensity 3, OC$\underline{H}_3$
$\delta = 3.78$ ppm, two doublets, intensity 1, J = 12 and 4 c/sec, OC$\underline{H}$—C(O)
$\delta = 4.70$ ppm, singlet, intensity 1, H$_3$COC$\underline{H}$ The 4-acetyl-2-methoxy-7,7-dimethyl-3-oxabicyclo[4.1.0]heptane had a purity of 98% and showed an $[\alpha]_D^{24} = 47.72$ (concentration 0.2 g/ml in benzene).

We claim:
1. A cis 4-Acetyl-2-alkoxy-7,7-dimethyl-3-oxabicyclo[4.1.0.]heptane wherein the alkoxy group contains from 1 to 5 carbon atoms.
2. A cis 4-Acetyl-2-methoxy-7,7-dimethyl-3-oxabicyclo[4.1.0]heptane.
3. The 1R,cis isomers of a compound according to claim 1.

* * * * *